United States Patent [19]

Grieger

[11] Patent Number: 4,575,249

[45] Date of Patent: Mar. 11, 1986

[54] METHOD AND DEVICE FOR MEASURING THE DENSITY OF COLOR LAYERS OF PRINTING INKS THAT ARE STILL WET

[75] Inventor: Dieter Grieger, Kiel, Fed. Rep. of Germany

[73] Assignee: Dr. Ing. Rudolf Hell GmbH, Fed. Rep. of Germany

[21] Appl. No.: 477,976

[22] Filed: Mar. 23, 1983

[30] Foreign Application Priority Data

Apr. 10, 1982 [EP] European Pat. Off. ........ 82103089.7

[51] Int. Cl.⁴ ............................................. G01N 21/47
[52] U.S. Cl. .................................... 356/369; 356/446
[58] Field of Search ............... 356/364, 369, 394, 395, 356/399, 446; 101/DIG. 24

[56] References Cited

U.S. PATENT DOCUMENTS 3,623,818  11/1971  Gardner et al. ..................... 356/369

OTHER PUBLICATIONS

Reisinger et al., "Alternative to Ellipsometry for Characterizing Transparent Thin Films", Optical Engineering, Jan./Feb. 1981, vol. 20, No. 1, pp. 111–114.

Primary Examiner—F. L. Evans
Attorney, Agent, or Firm—Hill, Van Santen, Steadman & Simpson

[57] ABSTRACT

A method and device for measuring the density of color layers of printing inks that are still wet is provided in which a polarized light source is directed toward the color layer along an axis of illumination which is inclined at the Brewster angle relative to the surface normal line of the color layer.

12 Claims, 1 Drawing Figure

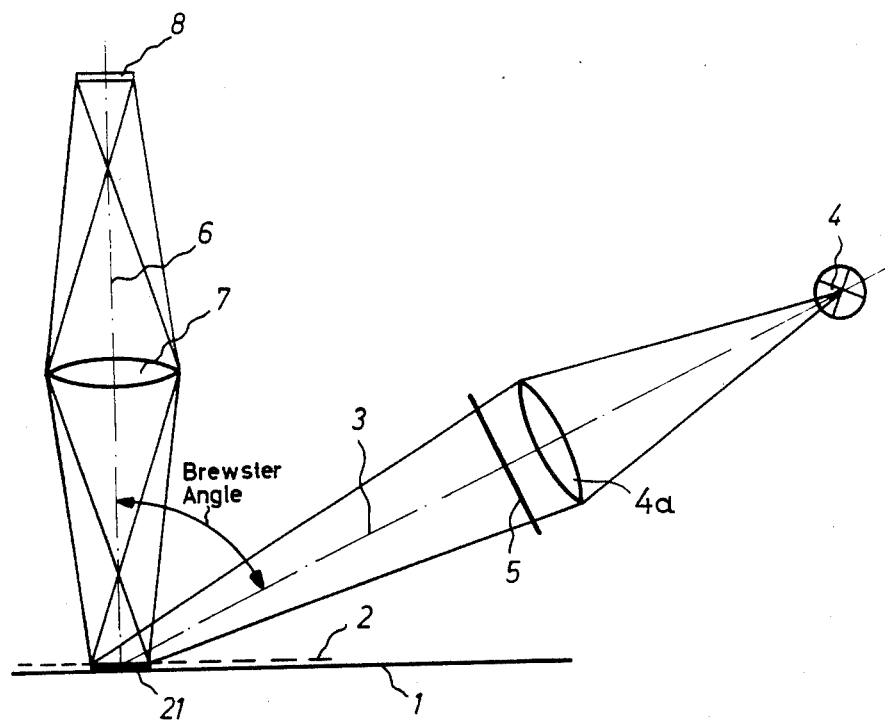

METHOD AND DEVICE FOR MEASURING THE DENSITY OF COLOR LAYERS OF PRINTING INKS THAT ARE STILL WET

BACKGROUND OF THE INVENTION

1. Field of the Invention

The invention relates to the field of printing technology and is particularly suited for densitometers and printing machines.

2. Description of the Prior Art

It is specified in the DIN draft No. 16536, DK 655.3062.12:535.65, April, 1979, part 2, 4.1, Measuring Geometry, that the light incidence for measurement in densitometric measuring should be directed at an angle of 45° relative to the surface normal line.

It has turned out, however, that in the measurement of densities of color layers of printing inks, the gloss of the ink which is still wet from printing falsifies the measurement when traditional densitometers are employed for measuring the specimens.

Further it is also necessary to continuously take density measurements of specimens for monitoring the color control in high-speed printing machines. This is necessary in order to be able to undertake a corresponding control or regulation of the amount of printing ink before the occurrence of inadmissible fluctuations in order to prevent these fluctuations.

If, given the measuring method taught in the prior art, one waits until the ink has been absorbed, then the operation to be regulated or controlled in, for example, the printing machine, occurs too late. That is, the regulation comes after an amount of spoilage has already arisen. Corresponding mis-measurements occur given the densitometer.

SUMMARY OF THE INVENTION

An object of the present invention is to specify a method and a device with which the measuring errors arising due to the gloss of the printing ink which is still wet are avoided.

The invention achieves this object by means of illuminating the wet ink layer with light polarized parallel to the plane of impingement at an angle approximately equal to the Brewster angle of the specific ink being applied, relative to the normal lines of the surface being inked. Specifically, the angle should be within the range of plus or minus 15% of the Brewster angle.

BRIEF DESCRIPTION OF THE DRAWINGS

The FIGURE is a schematic diagram of a device embodying the principles of the present invention.

DESCRIPTION OF THE PREFERRED EMBODIMENTS

A printing material 1 is illustrated in the FIGURE on which a layer 2 of printing ink which is still wet is applied. A wet color ink spot 21 to be measured is illuminated along an optical axis 3 by a light source 4. A lens 4a and a polarization filter 5 are disposed between the light source 4 and the wet color ink spot 21. The portion of the light reflected by the wet color ink spot 21 proceeds, given the illustrated arrangement, along a surface normal line 6 and through a lens 7 to a photocell 8 which converts the reflected light into an electrical testing current in a known manner.

The beam path 3 of the light emerging from the polarization filter 5 is disposed such that it approximately forms the Brewster angle with the surface normal line 6. It is thereby achieved that all light incident on the color ink layer 21 which is still wet is absorbed by said color ink layer and is diffusely re-emitted. The result of this is that, given this type of illumination, no lustrous effect occurs due to which light is usually eliminated for purposes of measurement. It has been found by experimentation that the Brewster angle need not be precisely observed and that the measuring installation still supplies satisfactory results when the angle of light incidence is within 15 percent of the Brewster angle.

The photocell 8 can preferably be disposed on the normal line 6 as shown in the FIGURE. However, this is not absolutely necessary since the light reflection from the wet color ink spot 21 is diffuse.

Further, this measuring method can also be used in connection with curvilinear printing surfaces, that is, not only as illustrated in the FIGURE, in which the printing surface is in a plane, but also within a printing machine in which the printing material 1 is located on a curved surface such as that of a printing drum.

The polarization direction of the polarization filter 5 is to be selected such that the E-Vector or electrical vector of the light waves passed by the filter oscillates parallel to the plane perpendicular to propagation and parallel to the plane formed by the normal line 6 and optical axis of the illumination beam path 3 (so-called p-waves or compression waves). The light to the polarization filter from the light source 4 can, for example, be directly supplied by means of a lamp or can also be supplied over optical wave guides or mirrors.

The Brewster angle of current commercially available printing inks has been determined to lie at 56°. At this angle, the reflectivity of the printing ink which is still wet is equal to zero for p-waves. Therefore, no light of the specimen illumination becomes unavailable due to lustrous effects, all light is defracted into the specimen and is diffusely reflected therefrom.

Thus, the same measured result is obtained immediately after ink application as well as after a time in which the ink has already been partially absorbed or dried, so that a precise measurement without the errors produced due to the luster effects is now possible in accord with the principles of this invention.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

The embodiments of the invention in which an exclusive property or privilege is claimed are defined as follows:

1. A method for measuring the density of color layers of printing ink which is still wet, comprising the steps of:
   (1) illuminating the color layer with a light source along an optical axis at an angle of impingement,
   (2) polarizing the light from the light source so that the E-Vector of the light is parallel to the plane of impingement defined by the optical axis and the surface normal line of the color layer, and
   (3) arranging the light source so that the angle of impingement relative to the surface normal line of the color layer is approximately the Brewster angle of the printing ink.

2. The method according to claim 1 in which the light source is arranged so that the angle of impingement relative to the surface normal line of the color layer is within a range of plus or minus 15% of the Brewster angle of the printing ink.

3. The method of claim 1 in which the light source is arranged so that the angle of impingement relative to the surface normal line of the color layer is exactly at the Brewster angle of the printing ink.

4. A device for measuring the density of color layers of printing ink which is still wet comprising:
   a source of polarized light for illuminating the color layer along an optical axis at an angle of incidence,
   the oscillation direction of the E-Vector of said polarized light being parallel to the plane of impingement which is defined by said optical axis and the surface normal line of the color layer,
   the optical axis of illumination being inclined relative to the surface normal line of the color layer at approximately the Brewster angle of the printing ink color layer, and
   a photoelectric receiver for measuring the light reflected by the color layer and converting the measured light into an electrical signal.

5. The device of claim 4 wherein the photoelectric receiver is disposed in the area of the normal line of the color layer.

6. The device of claim 4 wherein the optical axis of the illumination of the color layer is disposed in a range of plus or minus 15 percent around the Brewster angle of the printing ink relative to the surface normal line of the color layer.

7. The device of claim 6 wherein the photoelectric receiver is disposed in the area of the normal line of the color layer.

8. The device of claim 4 wherein the optical axis of the illumination of the color layer is disposed precisely at the Brewster angle of the printing ink relative to the surface normal line of the color layer.

9. The device of claim 8 wherein the photoelectric receiver is disposed in the area of the normal line of the color layer.

10. The device of claim 4 wherein said color layer is applied to a planar surface.

11. The device of claim 4 wherein said color layer is applied to a curvilinear surface.

12. A device for measuring the density of color layers of printing ink which is still wet comprising:
    a source of polarized light for illuminating the color layer along an optical axis,
    the oscillation direction of the E-Vector of said polarized light being parallel to the plane of impingement which is defined by the optical axis and the surface normal line of the color layer,
    the optical axis of illumination being inclined relative to the surface normal line to the surface of the color layer at approximately the Brewster angle of the printing ink,
    and a photoelectric receiver for measuring the light reflected by the color layer and converting the measured light into an electrical signal.

* * * * *